(12) United States Patent
Isshiki et al.

(10) Patent No.: US 7,090,697 B2
(45) Date of Patent: Aug. 15, 2006

(54) DEVICE FOR TREATING DYSPHONIA AND METHOD OF TREATING WITH USE OF THE SAME

(76) Inventors: Nobuhiko Isshiki, 22, Minami-Yonnotubo-cho, Iwakura, Sakyo-ku, Kyoto (JP) 606-0033; Ichiro Yamamoto, 2-3-8, Nigawa-cho, Nishinomiya-shi, Hyogo (JP) 662-0811

( * ) Notice: Subject to any disclaimer, the term of this patent is extended or adjusted under 35 U.S.C. 154(b) by 138 days.

(21) Appl. No.: 10/620,335

(22) Filed: Jul. 17, 2003

(65) Prior Publication Data
US 2004/0254642 A1 Dec. 16, 2004

(30) Foreign Application Priority Data
Jun. 11, 2003 (JP) .............................. 2003-165830

(51) Int. Cl.
*A61F 2/20* (2006.01)
(52) U.S. Cl. ........................................ 623/9; 623/11.11
(58) Field of Classification Search ................ 606/196, 606/199, 61; 623/9, 10, 11
See application file for complete search history.

(56) References Cited

U.S. PATENT DOCUMENTS 4,130,905 A * 12/1978 Mercandino ................. 623/10
5,549,673 A * 8/1996 Beale ............................. 623/9
5,836,948 A * 11/1998 Zucherman et al. .......... 606/61

OTHER PUBLICATIONS

N. Isshiki, "Vocal Mechanics as the Basis for Phonosurgery", *Laryngoscope* 108: Dec. 1998, pp. 1761-1766.
N. Isshiki, "Midline Lateralization Thyroplasty for Adductor Spasmodic Dysphonia", *Annals of Otology, Rhinology & Laryngology*, vol. 109, No. 2, Feb. 2000, pp. 187-193.
N. Isshiki, "Progress in Laryngeal Framework Surgery", *Acta Otolaryngol* 2000; 120, pp. 120-127.
N. Isshiki et al., "Thyroplasty for Adductor Spasmodic Dysphonia: Further Experiences", *Laryngoscope* 111: Apr. 2001, pp. 615-621.
H. H. Dedo, "Recurrent Laryngeal Nerve Section for Spastic Dysphonia", *Ann Otol Rhinol Laryngol*. 1976, 85, pp. 451-459.
M. F. Brin et al., "Treatment of Spasmodic Dysphonia (Laryngeal Dystonia) with Local Injections of Botulinum Toxin: Review and Technical Aspects", *Neurological Disorders of the Larynx*, N.Y. Thieme Medical Publishers, 1992; pp. 214-228.

* cited by examiner

*Primary Examiner*—Corrine McDermott
*Assistant Examiner*—Christopher Prone
(74) *Attorney, Agent, or Firm*—Bacon & Thomas, PLLC

(57) ABSTRACT

A device for treating spasmodic dysphonia (SD) and a surgical method of treating SD with use of the same are disclosed. The cause for SD is an excessively tight closure of the glottis. The device of the present invention is useful one for the surgery of thyroplasty type II which aims at widening the glottis. Use of the device may make the surgery easier, simpler, and shorter in time required.

9 Claims, 5 Drawing Sheets

DEVICE FOR TREATING DYSPHONIA AND METHOD OF TREATING WITH USE OF THE SAME

BACKGROUND OF THE INVENTION

1. Field of the Invention

The present invention relates to a surgical treatment for dysphonia and its requisite device for carrying out the treatment. More specifically, the invention relates to a device useful for the surgical treatment of thyroplasty type II, which has been known as Isshiki's operation, and a method of treating dysphonia with use of the device.

2. Discussion of the Related Art

The causes for difficulty of voice production or hoarse voice are multiple, for example vocal abuse, excessive smoking, vocal tumors such as polyp and cancer, and vocal fold mobility disturbance. Voice disturbance due to vocal abuse can be treated effectively by simple vocal rest for a week for instance, and dysphonia resulting from vocal tumors can be managed by surgical removal of the tumor. However, disphonia associated with vocal fold mobility disturbance, such as paralysis producing imperfect closure of the glottis, or conversely, excessively tight closure of the glottis on phonation is too complicated to handle by the above-mentioned treatments.

Spasmodic dysphonia, which is caused by an excessively tight closure of the glottis, was first treated by recurrent laryngeal nerve section, with some success, though proved later to be only temporary (see Dedo H H. Recurrent laryngeal nerve section for spastic dysphonia. Ann Otol Rhinol Laryngol. 1976; 85: 451–459). Recently, a treatment by administrating botulinum toxin to muscles of a patient was proposed as a replaceable therapy of the nerve section (see, Brin MF et al.: Treatment of spasmodic dysphonia (laryngeal dystonia) with local injections of botulinum toxin: in review and technical aspects. In A. Blitzer et al, eds.; Neurologic Disorders of the Larynx. New York, N.Y.: Thieme Medical Publishers 1992; 214–228). This approach with the administration of botulinum toxin is currently in most frequent use, however, there is a problem that the clinical efficacy of botulinum toxin dose not last in long term. Due to the fact that botulinum toxin induces temporary paralysis of the muscle where the toxin is injected, the effect of blocking the nerve impulse from the injection of the botulinum toxin gradually dwindles, usually diminishing in about 3 to 4 months. As a result, the patient requires an injection of the toxin every three to six months. To make matters worse, the repetitive injections of the toxin are associated with a serious problem that determination of the dose and injection site of the toxin is not easy due to great individual variation such as weight, age, and responsiveness to the therapy.

On the other hand, one of the inventors proposed a surgical intervention into the thyroid cartilage. As shown in FIG. 4, a part of the thyroid cartilage 11 forms the Adam's Apple. The proposed surgical treatment is called as thyroplasty type II and described in the articles "Isshiki N. et al.: Midline lateralization thyroplasty for adductor spasmodic dysphonia. Ann Otol Rhinol Laryngol 2000:109:189–193", and others.

The conventional surgical treatment of thyroplasty type II is carried out according as procedures in FIGS. 5 to 8. First, the thyroid cartilage 11 is vertically incised at the midline thereof (see FIG. 5), and the incised edges 11a, 11a are pulled laterally by hooks 12, 12 (see FIG. 6), so that the vocal folds are also pulled laterally, preventing excessive tight closure of the glottis.

After that, as shown in FIG. 7, a silicone prosthesis 13 is prepared. The silicone prosthesis 13 consists of a pair of wings 13b,13b and a prominence 13a between the wings 13b,13b, the prominence 13a being capable of fitting the width (W) of the groove 14 created by separation of the cartilage. The prominence 13a is inserted in the groove 14 and the pair of wings 13b,13b are fixed to the thyroid cartilage 11 by sutures, thereby securing the width (W) which is optimal distance for phonation. FIG. 8 illustrates that the two silicone prostheses 13,13 are fixed to the cartilage 11 at the upper and lower portions thereof.

This surgical procedure proved to be effective in relieving the vocal strain on phonation, recovering their normal voice in 26 patients operated on, with one exception who had other dystonia too. No recurrences were noted in any patient. The longest follow-up period is 4 years.

However, the procedure of fitting in and stabilizing the silicone prosthesis 13 in the groove 14 of the incised thyroid cartilage requires a surgical expertise. This technical difficulties prevented popularization of the surgical treatment of thyroplasty type II.

There is a further technical difficulty with the surgical treatment. Since the thyroid cartilage is located in the anterior middle of the neck, it is desirous that any protrusion after the procedure of fixing the silicone prosthesis 13 to the thyroid cartilage 11 is inconspicuous, especially in women. To meet the requirement, the silicone prosthesis 13 having small and thin wings 13a, 13a is preferably employed. On the other hand, numerous sutures are required in order to fix the prosthesis to the cartilage for long-term widening the incised edges of the thyroid cartilage, despite that such numerous sutures may cause damage to the edges of the incised cartilage and/or the thin silicone wings.

SUMMARY OF THE INVENTION

The object of this invention is to provide a device that allows easy technique when utilizing the thyroplasty for dysphonia, and may give a long lasting stable effect of restoring a normal voice.

The device for treating dysphonia of the invention comprises a pair of supporters for supporting edges incised at the midline of thyroid cartilage, and a connector for jointing the pair of supporters apart from each other. Both of the supporters and the connector are made of titanium or an alloy thereof.

In preferred embodiment of the invention, the device includes a connector having an adjustable width such that the distance (D) between the pair of supporters ranges from 2 to 6 mm.

One of an aspect of a method of treating disphonia of the invention uses the device of the invention and comprises the steps of incising thyroid cartilage at the midline thereof, keeping the incised edges of the thyroid cartilage transversely spaced apart from each other by such a sufficient distance as to prevent excessively tight closure of the glottis, and supporting the each edge by the corresponding supporter and securing the distance by inserting the connector between the edges.

Another aspect of a method of treating disphonia of the invention uses the device including a connector having an adjustable width. The method comprises the steps of incising thyroid cartilage at the midline thereof, supporting one of the incised edges of the thyroid cartilage by the corresponding supporter, and adjusting a width of the connector to a distance sufficient to prevent excessively tight closure of the glottis for fixation.

DETAILED DESCRIPTION OF THE INVENTION

Figure 1:
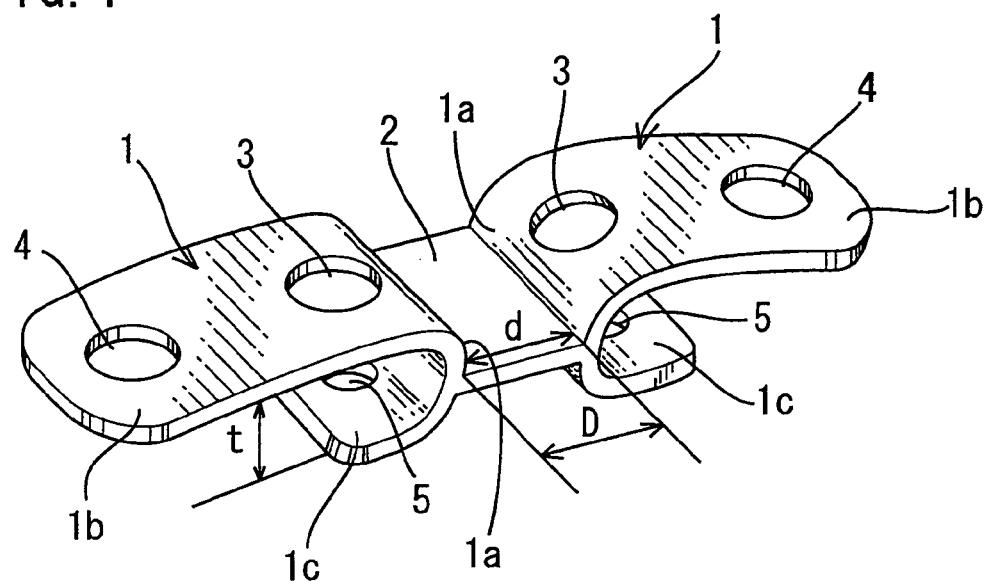
FIG. 1 is a perspective view showing one embodiment of the device of the present invention.

Referring to FIG. 1, there is provided a device for treating dysphonia of one embodiment of the present invention. The dysphonia treating device substantially consists of a pair of J-shaped supporters 1,1 and a connector 2 for jointing the supporters 1,1 apart from each other.

Each of the J-shaped supporters 1 is formed by bending a plate of titanium or an alloy thereof into two supporting parts 1b,1c having a different length from each other. A curved part 1a is formed between the two supporting parts 1b, 1c.

In a preferred embodiment of the invention, the shorter supporting part 1c to be disposed on a posterior part of the thyroid cartilage 11 has such a length from a corresponding one of the incised edges of thyroid cartilage to a distal end of the soft tissue behind the thyroid cartilage. Specifically, the length of the shorter supporting part 1c ranges from about 1.5 to about 3.5 mm. The length of the longer supporting part 1b to be disposed on an anterior part of the thyroid cartilage 11 is not limited as far as the longer supporting part 1b can sufficiently and securely support the thyroid cartilage 11 according to the shape thereof However, the length of the longer supporting part 1b preferably ranges from about 8 to about 12 mm.

According to the invention, the distance (t) between the longer supporting part 1b and the shorter supporting part 1c is preferably slightly larger than the thickness of the thyroid cartilage 11. Specifically, the distance (t) ranges from about 2 to about 4 mm. Too short a distance (t) will keep pressuring the cartilage to cause damage and/or tear of the cartilage, while too long distance (t) comparing with the thickness of the cartilage may result in slipping of the supporter 1 on the outer surface of the thyroid cartilage 11.

According to the preferable embodiment of the invention, two through-holes 3, 4 are formed in the longer supporting part 1b spaced apart from each other in a longitudinal direction of the longer part 1b to secure fastening of the device to the thyroid cartilage by way of suture. A through-hole 5 is formed in the shorter supporting part 1c at a position corresponding to the through-hole 3 to be disposed closer to the midline of the thyroid cartilage.

The connector 2 serves for jointing the pair of supporters 1, 1 spaced apart from each other by a certain distance. Lateral ends of the connector 2 are welded with top parts of the curved parts 1a, 1a, respectively in such a manner that the connector 2 may not be displaced from an imaginary line connecting the supporters 1, 1. The width (d) of the connector 2, namely, the distance (D) between the supporters 1,1 corresponds to a distance between the incised edges of thyroid cartilage. Generally, the distance (D) ranges from 2 to 6 mm depending on the individual requirement such as symptom, body type, and vocal condition of the patient.

The connector 2 as well as the supporters 1 is made of titanium or an alloy thereof. The titanium alloy may be any titanium alloy having biocompatibility such as used in artificial bone, artificial joint and artificial root of the tooth. Specifically, the titanium alloy free from Ni may be used, because Ni is suspected of being carcinogenic or allergen. Examples of such a titanium alloy free from Ni include Ti-6Al-4V which is known of its excellent biocompatibility. The titanium and the titanium alloy may be processed on the exterior surface thereof by N or C ions injection so as to prevent emission or abrasion of the metal itself.

Figure 2:
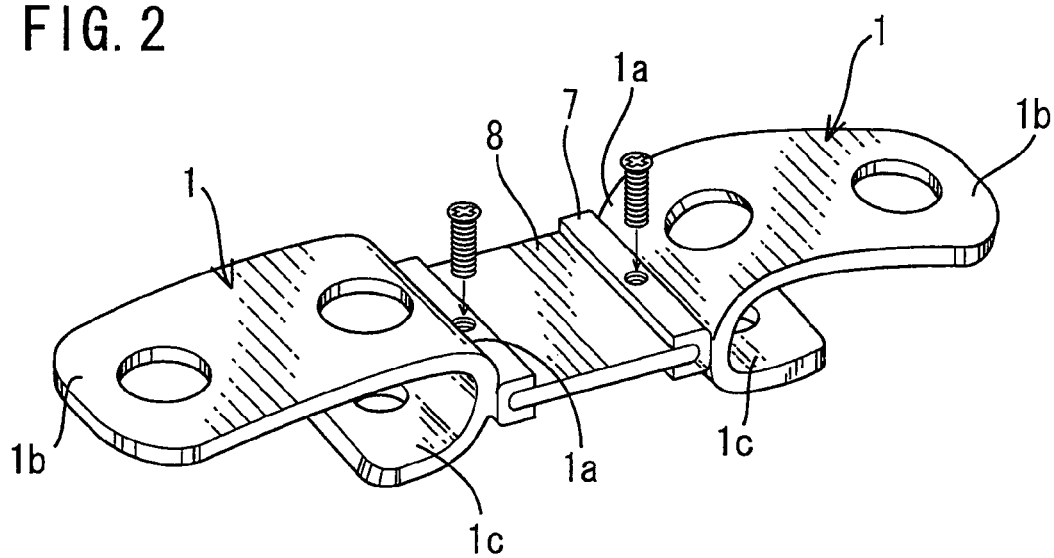
FIG. 2 is a perspective view showing one embodiment of the inventive device including an adjustable connector.

In the embodiment shown in FIG. 1, the connector 2 is integrally mounted on the supporters 1, 1 in a state that the width (d) of the connector 2 is fixed, but not limited thereto. The preferred embodiment of the device may include a connector such that the width (d) of the connector is adjustable so that the device is applicable to various types of patients. An example of such a preferable embodiment is shown in FIG. 2. The device shown in FIG. 2 comprises a pair of J-shaped supporters 1,1 each having U-shaped holder 7 to an outer surface of the curved part 1a thereof, and a connector 8 which is separately formed of the supporters 1,1. Lateral ends of the connector 8 is held into respective U-shaped recesses of the holders 7, 7 and fixed by screws. Pins may be used instead of screws. The connector 8 has such a width as to secure a desired distance (D) between the supporters 1, 1 by selecting and arranging the optimum size for fixation. In accordance with the embodiment of the device including a width-adjustable connector 8, merely preparing titanium plates of various widths makes it possible to desirably adjust the distance (D) between the supporters 1,1.

Next, a method of treating disophonia of the present invention will be described.

One aspect of the treating method of the invention uses the device shown in FIG. 1 and is conducted as follows.

Figure 3:
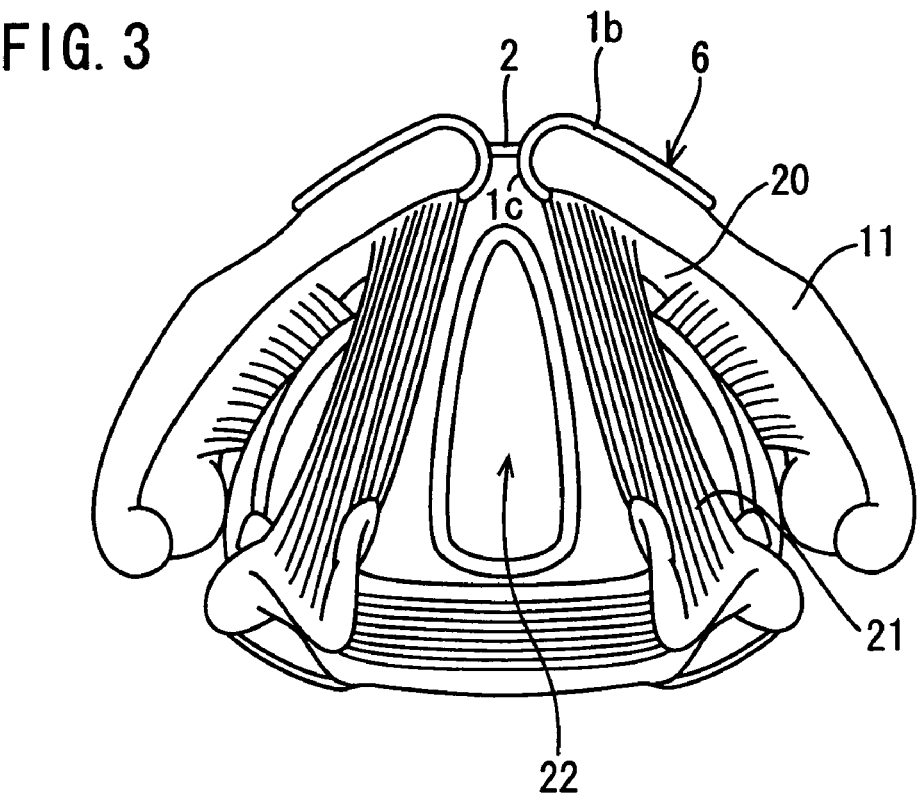
FIG. 3 schematically shows the device of the invention applied to the thyroid cartilage.
Figure 4:
FIG. 4 illustrates the related laryngeal anatomy.
Figure 5:
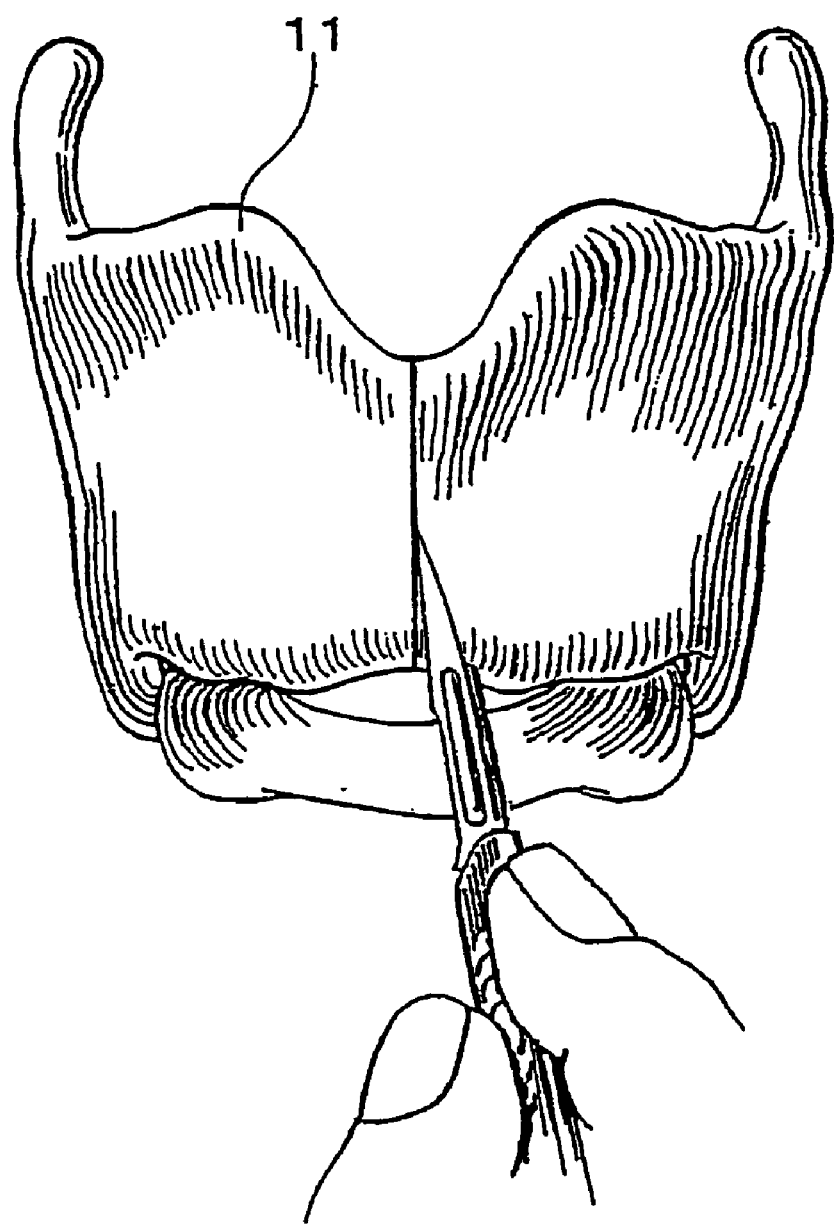
FIG. 5 illustrates the initial procedure of surgical treatment of the thyroplasty type II.
Figure 6:
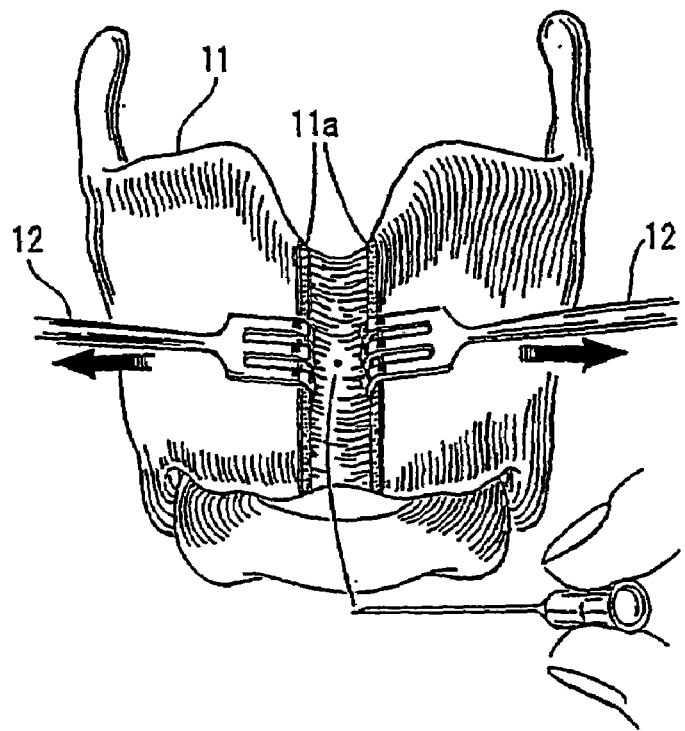
FIG. 6 illustrates the second procedure of the surgical treatment of thyroplasty type II, wherein the incised edges are pulled laterally.
Figure 7:
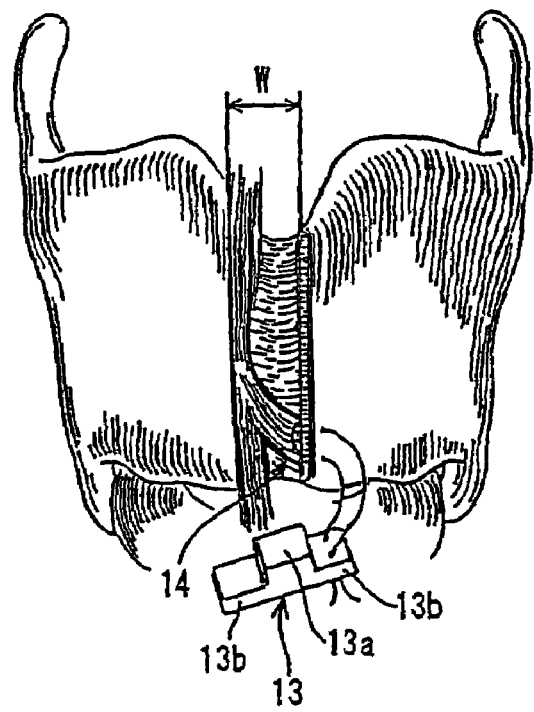
FIG. 7 illustrates the third procedure of the conventional surgical treatment of thyroplasty type II, wherein the prominence of silicone prosthesis is inserted between the incised edges.
Figure 8:
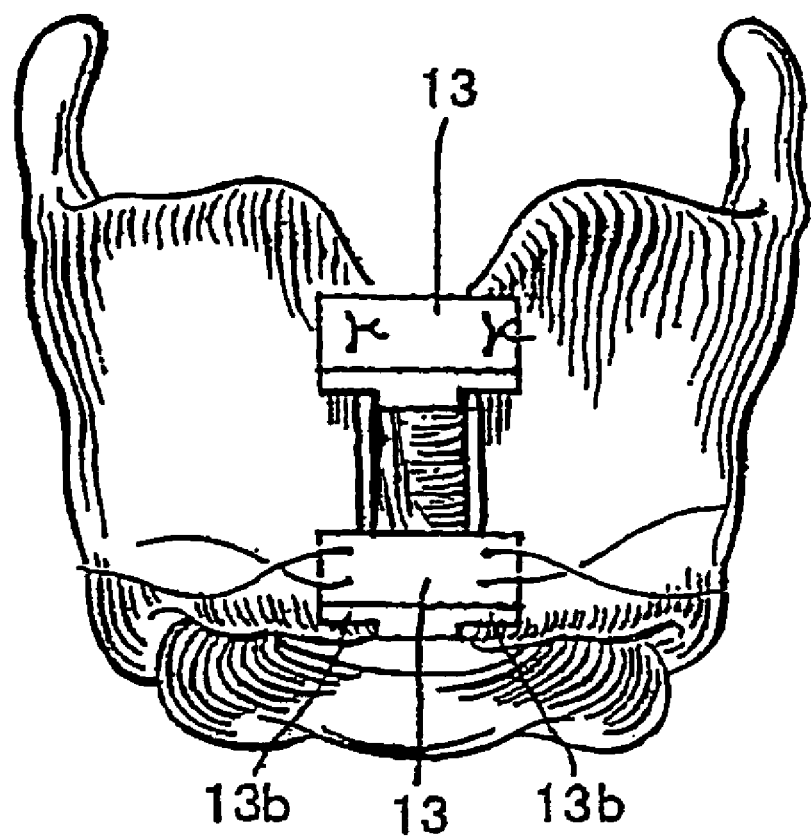
FIG. 8 illustrates the final scene of the conventional surgical treatment of thyroplasty type II, wherein the two silicone prostheses are fixed to the thyroid cartilage.

First, the thyroid cartilage is exposed and the cartilage is incised at the midline thereof (see FIG. 5), and the incised edges 11a,11a are separated laterally (see FIG. 6). This procedure results in widening of the glottis, relieving tight glottal closure on phonation. After determining the optimal width (W) of the separation of the incised edges 11a, 11a, a device including a connector 2 having its width fitting to the width (W) of the incised edge is chosen. The optimum device is applied to the thyroid cartilage 11 by supporting the respective incised edges by the corresponding supporter 1. As shown in FIG. 3, the device 6 is applied such that the longer supporting part 1b is disposed on an anterior part of the thyroid cartilage 11 and shorter supporting part 1c is disposed on a posterior part of the thyroid cartilage 11.

The shorter supporting part 1c easily slips into the space created by undermining between the cartilage 11 and the soft tissue 20, because the part 1c is formed of the very thin titanium plate.

Fixation of the device 6 is enhanced by the sutures, passing through the through-holes 3,5 of the each supporter 1. Firmer fixation may be implemented by additional suture through the posterior through-hole 4 of the each longer supporting part 1b. These suturing procedures can be carried out much easier than fixation suture for silicone prosthesis, because the cartilage is already almost fixed by the supporters 1,1. Under the condition applied the device 6 to the thyroid cartilage, the glottis 22 is almost permanently widened by the connector 2 of the device 6. In FIG. 3, the thyroarytenoid muscle is represented as 21.

According to the present invention, in case that the device including the connector having adjustable width is used, the treating method comprises the steps of incising thyroid cartilage at the midline thereof, supporting one of the incised edges of the thyroid cartilage by the corresponding supporter, and adjusting a width of the connector to a distance sufficient to prevent excessively tight closure of the glottis for fixation.

The step of adjusting and determining a width of the connector may be executed either before or after the step of supporting the incised edges by the supporters. In case of using the device shown in FIG. 2, it is preferable that after adjusting the connector to the optimum width thereof, the supporting step is executed by mounting the adjusted device to the thyroid cartilage.

When a small perforation develops near the anterior commissure while carrying out the surgical treatment of this invention, the perforation may be closed by the sternohyoid muscle flap, just as it is in the conventional thyroplasty type II.

As described above, the device of the invention allows the surgical treatment of the thyroplasty type II simpler and easier, and brings about better outcomes as compared with the case of using a silicone prosthesis It implies the thyroplasty type II for spasmodic dysphonia is no longer the surgery that requires special skill, and will be popularized. Furthermore, the device made of titanium or an alloy seems to be superior to a silicone prosthesis in biocompatibility and strength, and therefore promises a long stable effect favorable for voice. Still furthermore, the less pressure imposed on the cartilage which is in contact with the device, the less damage on the cartilage edges. Accordingly, the surgery treatment of the present invention brings about almost permanent relief of the patients from the strain of speech. And there is no problem associated with appearance in the neck region after operation.

The surgical treating method of the invention is efficient for particularly spasmodic dysphonia, which is featured by excessively tight closure of the glottis (aperture formed by the vocal folds), causing unintentional sudden stoppage or tremor of voice. The spasmodic dysphonia can be classified into 3 types; adductor type (excessive adduction on phonation), abductor type (the vocal folds abduct on phonation), and the mixed type. Among these, most frequent is the adductor type (adductor spasmodic dysphonia, ADSD). The treating method of this invention is righteously useful for this most frequent ADSD. Briefly, this inventive surgical treatment of thyroplasty type II is effective for any dysphonia caused by excessively tight closure of the glottis.

EXAMPLE

A 31 years old woman with ADSD underwent, with the consent of the patient, the thyroplasty type II using the device shown in FIG. 1 in place of silicone prosthesis. The supporters support the incised cartilages in stable condition that made the suture procedures much easier than otherwise.

Postoperatively, the voice has been restored to normal without any stress-strain. Furthermore, neither unnatural elevation nor marked scar has been noted in the neck region, to the patient satisfaction. No recurrence of any kind is noted 4 months after operation.

This application is based on patent No. 2003-165830 filed on Jun. 11, 2003 in Japan, the contents of which hereby incorporated by reference.

What is claimed is:

1. A device for treating dysphonia comprising:
   a pair of substantially J-shaped supporters each made of a plate of titanium or an alloy thereof for supporting a corresponding one of edges incised at the midline of thyroid cartilage; and
   a connector made of a plate of titanium or an alloy thereof, for joining the pair of supporters apart from each other,
   wherein the J-shaped supporter has a longer supporting part of about 8 mm to about 12 mm in length and a shorter supporting part of about 1.5 mm to about 3.5 mm in length, and the connector has a width (d) of from 2 mm to 6 mm and is fixed with the respective curved portion of the J-shaped supporters.

2. The device according to claim 1, wherein the alloy has biocompatibility.

3. The device according to claim 1, wherein said each J-shaped supporter consists of a shorter supporting part to be disposed on an anterior part of the thyroid cartilage and a longer supporting part to be disposed on a posterior part of the thyroid, and the shorter supporting part is spaced apart from the longer supporting part by a distance (t) ranging fro 2 to 4 mm.

4. The device according to claim 1, wherein each supporter is formed with through-hole for passing suture therethrough.

5. The device according to claim 1, wherein said J-shaped supporters have substantially the same shape and size as each other.

6. A device for treating dysphonia comprising:
   a pair of substantially J-shaped supporters each made of a plate of titanium or an alloy thereof for supporting a corresponding one of edges incised at the midline of thyroid cartilage; and
   a connector made of a plate of titanium or an alloy thereof, for joining the pair of supporters apart from each other,
   wherein the J-shaped supporter has a longer supporting part of about 8 mm to about 12 mm in length and a shorter supporting part of about 1.5 mm to about 3.5 mm, the J-shaped supporters form mirror images of each other, and the connector has a width (d) of from 2 mm to 6 mm and is fixed with the respective curved portion of the J-shaped supporters.

7. The device according to claim 6, wherein the alloy has biocompatibility.

8. The device according to claim 6, wherein the shorter supporting part is disposed on an anterior part of the thyroid cartilage the longer supporting part is disposed on a posterior part of the thyroid, and the shorter supporting part is spaced apart from the longer supporting part by a distance (t) ranging fro 2 to 4 mm.

9. The device according to claim 6, wherein each supporter is formed with through-hole for passing suture there through.

* * * * *